United States Patent [19]
Boos et al.

[11] Patent Number: 6,103,126
[45] Date of Patent: Aug. 15, 2000

[54] PROCESS FOR THE SELECTIVE ELIMINATION OF INORGANIC PHOSPHATE FROM LIQUIDS BY MEANS OF ABSORBENT MATERIALS MODIFIED WITH POLYNUCLEAR METAL OXYHYDROXIDES

[75] Inventors: Karl-Siegfried Boos, Gauting; Dietrich Seidel, Feldafing; Klaus Spengler, Niedenstein-Kirchberg; Gudrun Henke, Melsungen; Andreas Rauh, Kassel, all of Germany

[73] Assignee: SeBo GmbH, Erbach, Germany

[21] Appl. No.: 09/145,129

[22] Filed: Sep. 1, 1998

Related U.S. Application Data

[62] Division of application No. 08/720,925, Oct. 7, 1996, Pat. No. 5,846,426, which is a continuation of application No. 08/452,397, May 26, 1995, abandoned, which is a division of application No. 08/417,844, Apr. 6, 1995, Pat. No. 5,514,281, which is a continuation of application No. 08/153,567, Nov. 17, 1993, abandoned.

[30] Foreign Application Priority Data

Nov. 24, 1992 [DE] Germany .............................. 42 39 442

[51] Int. Cl.[7] .............................. A61M 1/36; A61K 33/06; A61K 33/26; C08B 37/02
[52] U.S. Cl. .......................... 210/645; 210/504; 210/506; 424/646; 424/647; 424/648; 424/682; 536/113; 604/4
[58] Field of Search ..................................... 210/645, 504, 210/506; 604/4, 6; 424/646, 647, 648, 682; 435/103; 536/113

[56] References Cited

U.S. PATENT DOCUMENTS

| 2,885,393 | 5/1959 | Herb ........................................ 536/113 |
| 3,697,502 | 10/1972 | Christensen ............................ 536/113 |
| 4,180,567 | 12/1979 | Herb ........................................ 536/113 |
| 4,569,836 | 2/1986 | Gordon .................................. 128/205 |
| 4,599,405 | 7/1986 | Müller et al. ............................ 536/113 |
| 4,827,945 | 5/1989 | Groman et al. ............................. 424/4 |
| 4,828,843 | 5/1989 | Pich et al. ............................... 424/480 |
| 4,927,756 | 5/1990 | Schwengers ............................ 435/103 |
| 4,970,079 | 11/1990 | Hem et al. .............................. 424/626 |
| 5,043,101 | 8/1991 | Gordon .................................. 536/113 |
| 5,055,288 | 10/1991 | Lewis et al. ............................ 536/113 |
| 5,234,697 | 8/1993 | Sopos ..................................... 424/490 |
| 5,492,814 | 2/1996 | Weissleder .............................. 436/173 |

OTHER PUBLICATIONS

H. Burt et al., *Journal of Pharmaceutcal Sources*, "Ion Exchange Resins as Potential Phosphate–Binding Agents for Renal Failure Patients: Effect of Physicochemical Properties of Resins on Phosphate and Bile Salt Binding", vol. 76, No. 5, May 1987.

G. Herca et al., Prevention of phosphate retention and hyperphosphatemia uremia, *Kidney International*, vol. 32, Suppl. 22 (1987), pp. S–215–S–220.

(List continued on next page.)

*Primary Examiner*—John Kim
*Attorney, Agent, or Firm*—Arent Fox Kintner Plotkin & Kahn, PLLC

[57] ABSTRACT

The present invention concerns the use of an adsorbent material modified with polynuclear metal oxyhydroxides for the selective elimination of inorganic phosphate from liquids, in particular from body fluids containing protein such as whole blood, plasma, liquid contents of the intestine as well as from dialysis fluid, as well as a process for the production of a pharmaceutical agent for oral application for the selective removal of inorganic phosphate in which an adsorbent material used according to the present invention, as such or pressed into powder form, is coated with a layer resistant to gastric acid or dispensed into an acid-resistant capsule. In order to selectively eliminate inorganic phosphate in an extracorporeal perfusion system, a body fluid such as whole blood or plasma is passed over one of the adsorbent materials.

17 Claims, 2 Drawing Sheets

ADSORBENT 1 = HS
ADSORBENT 2 = PL

OTHER PUBLICATIONS

W.H. Jones et al., *Journal of Pharmaceutical*, Quantification of the Binding Tendencies of Cholestyramine III: Rates of Adsorption of Conjugated Bile Salt Anions onto Cholestyramine as a Function of Added Inorganic Electrolyte Concentration, Temperature, and Agitation Intensity, vol. 59, No. 6, Jun. 1970.

S. Hjertén et al., *Journal of Chromatography*, "High-performance absorption chromatography of proteins on deformed non-porous agarose beads coated with insoluble metal compounds I" 481 (1989) pp. 175–186.

S. Hjertén et al., *Journal of Chromatography*, "High-performance absorption chromatography of proteins on deformed non-porous agarose beads coated with insoluble metal compounds II" 481 (1989) pp. 187–199.

Müller, *Arzneimittel–Forschung*, "Makromolekulare Eisen (III)–Hydroxid Komplexe.", vol. 17, No. 8, Aug. 1967.

S. Budavari et al., *The Merck Index*, 11th Edition, 1989, Merck & Co.

Eybl et al., *Acta Pharmacologica et Toxicologica*, "Interaction of Chelating Agents, Ferric Dextran and Zinc with indium in mice.", vol. 59, (1986), pp. 457–477.

D. Choy et al., *International Journal of Nuclear Medicine and Biology*, "The effective of iron–dextran on the biodistribution of technetium pyrophosphate", vol. 9, (1982) pp. 277–282.

Heldenberg et al., *The American Journal of Clinical Nutrition*, "Effect of iron on serum 25–hydroxyvitamin D and 24, 25 dihydroxyvitamin D concentrations.", vol. 56, No. 3, Sep. 1992, pp. 533–536.

Boudinot et al., *Journal of Pharmaceutical Sciences*, "Fluid shifts and other factors affecting plasma protein binding of prednisolone by Equilibrium dialysis", vol. 73, No. 6, Jun. 1994, pp. 774–780.

Nova et al., *American Journal of Nursing*, "Dialyzable Drugs", vol. 87, No. 7, Jul. 1987, pp. 933–942.

Database WPI, Section CH, Week 8522, Derwent Publication, Ltd.

PROCESS FOR THE SELECTIVE ELIMINATION OF INORGANIC PHOSPHATE FROM LIQUIDS BY MEANS OF ABSORBENT MATERIALS MODIFIED WITH POLYNUCLEAR METAL OXYHYDROXIDES

This is a divisional of U.S. Ser. No. 08/720,925 filed Oct. 7, 1996, U.S. Pat. No. 5,846,426; which is a continuation of U.S. Ser. No. 08/452,397 filed May 26, 1995, abandoned, which is a divisional of U.S. Ser. No. 08/417,844 filed Apr. 6, 1995, now U.S. Pat. No. 5,514,281, which is a continuation of U.S. Ser. No. 08/153,567 filed Nov. 17, 1993, abandoned.

DESCRIPTION

The invention concerns the selective elimination of inorganic phosphate from liquids, in particular from body fluids containing protein such as whole blood, plasma, liquid contents of the intestine as well as from dialysis fluid and the production of a pharmaceutical agent suitable for this.

It is well known that patients with chronic renal insufficiency can be successfully treated for years with the aid of dialysis (haemodialysis or peritoneal dialysis; artificial kidney) and thus be kept alive for a long tire period. Substances usually eliminated with the urine are removed by the artificial kidney over a semipermeable membrane. The quality and quantity of substance transport in this process is determined by a number of factors such as the surface area, the structure and thickness of the dialysis membrane, the flow rates of the washing solution (dialysis fluid) and of the blood, the ultrafiltration rate, the duration of the dialysis treatment, the difference in concentration of the dialysable substances between blood and washing solution as well as the molecular size and form of the dialysable substances.

However, during the course of a long-term haemodialysis complications often occur which are characteristic for this group of patients. Thus renal osteopathy is one of the serious long-term complications. This disease not only considerably impairs the general state of health of the dialysis patient but he is additionally also threatened with invalidity. One component of this clinical picture is secondary hyperparathyroidism which is associated with uraemic hyperphosphataemia. The chronic accumulation of phosphate in dialysis patients leads to highly increased serum concentrations of inorganic phosphorus (more than 6 mg/dl) and is due to reduced phosphate clearance by the dialysis membrane.

A primary aim of prophylactic and therapeutic measures in patients with renal osteodystrophy is therefore to lower the level of serum phosphate below a threshold value of 1.8 mmol/l (5.6 mg phosphorus/dl). A dietary restriction of the phosphate intake and thereby an effective lowering of the level of serum phosphate is limited it not impossible in long-term therapy since there is the risk of an inadequate protein intake and thus of malnutrition. Thus for example on an average dietary phosphate intake of 3.8 to 4.7 g/day only about 1 g phosphate per day can be eliminated by dialysis (haemodialysis or peritoneal dialysis). Thus the patients have an undesired positive phosphate balance despite the restriction (Hercz, G. et al., Kidney Int. Suppl. 22 (1987), 215–220).

For this reason phosphate binding agents that can be administered orally are preferably used as therapeutic agents which are intended to prevent the resorption of food phosphates in the gastrointestinal tract. Known substances with phosphate-binding properties are calcium salts (e.g. calcium acetate, calcium carbonate, calcium citrate, calcium alginate, calcium gluconate, calcium lactate and calcium sulfate), magnesium carbonate and magnesium hydroxide as well as aluminium hydroxide and aluminium carbonate. However, not all of these salts have gained therapeutic importance. Aluminium hydroxide (e.g. Antiphosphate®, Gry Pharma GmbH), calcium carbonate and calcium acetate (U.S. Pat. No. 4,870,105 (1989)) are in use. However, These agents for enteric phosphate restriction have undesired side effects. Thus when $Al^{3+}$ compounds are administered chronically a microcytic anaemia or encephalopathy can develop with a very poor prognosis or osteopathies occur. Major disadvantages of a long-term therapy with calcium salts are the development of a pronounced hypercalcaemia which is associated with calcification of blood vessels and soft tissues and gastrointestinal complaints (Dialyse Journal 37 (1991), 1–40).

Apart from these salt-like phosphate binding agents, a macroporcus sorbent is known from DE 28 15 811 C2 (1978) which is characterized in that it is an organic cation exchanger which is loaded with ions of at least one metal whose phosphate is only poorly soluble. However, this sorbent is only suitable for removing phosphate from protein-free liquids (e.g. dialysis fluid) since when it is used in an extracorporeal system for the elimination of phosphate from whole blood or plasma it releases the ionically bound metal ions in an undesired manner (see comparative example 10).

In addition Burt, H. M. et al. (J. Pharm. Sci. 75 (1987), 379–383) describe anion exchangers based on DOWEX® which carry tertiary or quarternary amines as the functional group and adsorb inorganic phosphate in the intestinal tract. However, it is known that strongly basic anion exchangers such as for example cholestyramine (Johns, W. H., Bates, T. R., J. Pharm. Sci. 59 (1970), 788 ff.) also undesirably bind bile acids and hence their long-term use leads to hypovitaminosis.

An object of the present invention is therefore to provide adsorber materials which are improved compared to the state of the art and allow a selective removal of inorganic phosphate, which generally occurs in the form of $HPO_4^{2-}$ and $H_2PO_4^-$, from aqueous liquids and in particular from body fluids containing protein such as for example whole blood, plasma and intestinal contents. In this process the other components of the liquid to be treated should not interact with the adsorbent materials in an undesirable or damaging manner for the patient. In addition the binding capacity of the adsorbent for phosphate should satisfy optimal practical (therapeutic) requirements and it must be possible to sterilize the adsorbent material with heat or/and gamma rays.

This object is achieved according to the present invention by using an adsorbent material modified with polynuclear metal oxyhydroxides for the selective elimination of inorganic phosphate from liquids, in particular from body fluids containing protein such as whole blood, plasma, liquid contents of the intestine as well as from dialysis fluid.

Adsorbent materials modified with polynuclear metal oxyhydroxides are known. The production of non-porous agarose particles coated with polynuclear metal oxyhydroxides is described in the Journal of Chromatography, Volume 481 (1989), 175–199, S. Hjerten and coauthors. However, the authors only use these particles as chromatographic support materials for the analytical separation of protein mixtures. For this purpose the metal oxyhydroxide-coated agarose particles are equilibrated with a phosphate solution and by this means are converted into the metal oxyhydroxide-phosphate species necessary for the desired separation efficiency. It does not teach a therapeutic application for these adsorbent materials.

The use of polynuclear iron(III) oxyhydroxide-polyol complexes as aqueous solutions in veterinary medicine for parenteral therapy of iron deficiency is also known. The production and structure of such macromolecular iron(III) oxyhydroxide complexes is described by A. Müller ("Arzneimittelforschung, Vol. 8 (1967), 921–931). A therapeutic application for the selective removal of inorganic phosphate from body fluids is not proposed.

In contrast to using anion or cation exchangers which are already known and are mentioned above, the use of adsorbent materials according to the present invention has the surprising advantage that they bind inorganic phosphate with high affinity. The elimination of phosphate is therefore independent of their concentration in the liquid to be treated (examples 5, 6, 8, 9). This property is of particular advantage for medical purposes since this enables a controlled and therapeutically adequate elimination of inorganic phosphate which could previously not be carried out.

In the production of adsorbent materials modified with polynuclear metal oxyhydroxides for the application according to the present invention one must take care that oxygen bridges are formed between different metal atoms. For this purpose either firstly the polynuclear metal oxyhydroxide can be prepared and then linked to the base material or it is preferably prepared on the base material itself and namely by impregnating the base material with a suspension, or particularly preferably a solution, of a suitable metal salt and subsequently increasing the pH value to strongly alkaline conditions (pH$\geq$10), if desired, while heating. The production of water-soluble iron-dextran is described for example in U.S. Pat. No. 4,927,756. All supports suitable according to the present invention can be produced in an analogous manner. It is important for the stable binding of the metal to the base material that there are sufficient free reactive groups located on it which are preferably organic or/and inorganic OH groups.

Any porous base material can be used as the starting material for the production of support materials modified with polynuclear oxyhydroxides. However, it is preferable to use supports which have organic or/and inorganic hydroxyl groups (OH groups). Thus or example organic supports such as cross-linked carbohydrates, organic polymers or copolymers, natural, semisynthetic or synthetic linear or/and branch-chained, soluble or insoluble polyhydroxyl compounds e.g. agarose, dextran, dextrin, cellulose or/and polyvinyl alcohol can be used as the base material. Specific examples are Trisacryl GF (cross-linked N-acryloyl-2-amino-2-hydroxymethyl-1,3-propanediol; LKB Produkter AB Co., Bromma, Sweden), TSK gels (copolymers of ethylene glycol, glycidylmethacrylate and pentaerythritoldimethacrylate, e.g. TSK HW 65; E. Merck Co. Darmstadt), cross-linked agarose (e.g. Sepharose; Pharmacia Co., Uppsala, Sweden), cellulose gels (e.g. Sephacel, Pharmacia Co., Uppsala, Sweden). On the other hand one can also use inorganic supports, in particular those based on silicon dioxide or/and silicates such as glyceryl-modified glasses (e.g. Bioran®-CPG, OH modification; Schott Glaswerke Co., Mainz) and glyceryl-modified silica gels (e.g. LiChroprep-Diol, E. Merck Co., Darmstadt).

The following are preferably used according to the present invention: a saponified copolymer of vinyl acetate and divinylethylene urea (VA-hydroxy Biosynth®, Riedel de Haen Co., Seelze) (example 2), copolymers of the Lewatit R series (e.g. Lewatit R 249-K; Bayer AG Co., Leverkusen) (example 3) and inorganic (silica gel, glasses) or organic porous supports modified with dextran (molecular weight: $5\times10^3$–$5\times10^6$ Daltons) according to methods known to a person skilled in the art.

Particularly preferred starting materials are dextran gels (example 1) such as products of the Dormagel N® series (Pfeiffer & Langen Co., Dormagen) which have an average molecular exclusion limit of $10^2$ to $10^6$, preferably less than $10^4$ Daltons. Coupling to dextran can for example be carried out according to the methods described in Affinity Chromatography, IRL Press, Oxford (1985).

The base material for the modified adsorbent material is preferably a porous particulate substance which has an average particle size of between 5 and 500 μm.

A large number of metals are suitable for use as polynuclear metal oxyhydroxides such as all transition metals such as zirconium and also aluminium. However, iron is used as a particularly preferred metal since, should a small release of the metal occur, iron is the one metal which may be regarded as being least harmful for the body. Therefore trivalent iron is most preferred as the metal for physiological reasons although other metals can also be used based on their binding properties with regard to inorganic phosphate.

A surprising feature of the adsorbent materials used according to the present invention is that the polynuclear metal oxyhydroxide or metal ion covalently or coordinatively bound to the support and in particular the preferably used iron(III) compound is not released by them to a significant extent even when they are contacted with liquids containing protein such as for example whole blood and/or plasma (see examples 7 and 10) and thus they do not cause any undesired side-effects such as a disturbance of enteric iron resorption or of cellular and in particular of erythrocytic iron metabolism in a therapeutic extracorporeal or/and oral application according to the present invention.

Moreover the adsorbent materials used according to the present invention do not interact in an undesirable manner with the other components of body fluids and for example do not cause an activation of the coagulation system or an haemolysis when contacted with whole blood (examples 7, 8). Adsorbent materials used according to the present invention are therefore suitable in a particularly advantageous manner for the selective elimination of inorganic phosphate from body fluids such as plasma or/and whole blood in an extracorporeal perfusion system in the case of hyperphosphataemia caused by dialysis or from dialysis fluid. This whole blood compatibility is of great interest from a medical and therapeutic point of view since this enables the elimination of phosphate concurrently with haemodialysis treatment (example 9). This therefore obviates the need for expensive and complex devices for separating and returning erythrocytes and a substantial simplification and reduction in the cost of the method is achieved. Supporting materials with an average particle diameter of 100 to 500 μm, particularly preferably 200 to 500 μm, are preferably used in an extracorporeal perfusion system for the application according to the present invention.

Thus the present invention also concerns a process for the selective elimination of inorganic phosphate from body fluids such as whole blood or/and plasma in an extracorporeal perfusion system or from dialysis fluid which is characterized in that the liquid to be treated is passed over an adsorbent material modified with a polynuclear metal oxyhydroxide preferably Fe(III) oxyhydroxide.

Accordingly the present invention also in addition concerns a device for the medical-therapeutic extracorporeal removal of inorganic phosphate from aqueous liquids, in particular from dialysis fluid, whole blood or/and plasma. This device comprises a preferably cylindrical housing provided with an inlet and outlet which is filled with an adsorbent material modified with polynuclear metal oxyhydroxides. The front ends of the housing are preferably provided with caps which each have a central inlet and outlet tube (example 9). It is particularly preferable that this cylindrical housing has a diameter of 3 to 20 cm, preferably 5 to 10 cm and a length of 1 to 40 cm, preferably 10 to 20 cm. The preferred material for the housing is glass or plastic.

Sieves with a pore size of 10 to 300 $\mu$m are integrated into this device according to the present invention and preferably in the caps of the cylindrical housing to eliminate particles. The device according to the present invention can be sterilized in a package by means of radiation (e.g. gamma rays) or by heat (example 4) and is thus particularly suitable for use in an extracorporeal perfusion system or/and for the purification of dialysis fluid.

A further embodiment of the invention concerns the use of the adsorbent materials in the form of oral preparations for the enteric adsorption or elimination of inorganic phosphate. Particularly advantageous features for an oral form of administration have proven to be the irreversible binding property and binding capacity which can thus be easily controlled via the dose, the neutral taste and the simple galenic formulation. For this purpose the adsorbent materials used according to the present invention, with a particle size of 5 to 200 $\mu$m, preferably 5 to 20 $\mu$m or/and pressed as a powder using methods known to a person skilled in the art, are coated with a layer resistant to gastric acid (e.g. Eudragit L 30 D, Röhm Pharma Co., Weiterstadt) or dispensed into acid-resistant capsules.

Thus the present invention also concerns a process for the production of a pharmaceutical agent for oral administration for the selective removal of inorganic phosphate which is characterized in that an adsorbent material modified with polynuclear metal hydroxides, as such or pressed into a powder form, is coated with a layer resistant to gastric acid or dispensed into an acid-resistant capsule.

For the oral application according to the present invention support materials are preferably used with an average particle diameter of 5 to 200 $\mu$m, preferably 5 to 20 $\mu$m.

For the oral use according to the present invention of polynuclear metal oxyhydroxide-polyol complexes it is also possible to use the corresponding polyol structural elements of the cross-linked polysaccharide support such as for example agarose, dextran, dextrin, detran derivatives, cellulose and cellulose derivatives. Comparable preparations are commercially available as iron(III) compounds and are used as anti-anaemia agents in iron deficiency (e.g. Dormafer®, Ferrum-Hausmann®). The soluble metal oxyhydroxide-polyol complexes are able to adsorb phosphate or phosphorus from aqueous phosphate solutions as well as from standardized intestinal contents in a quantitative and irreversible manner (examples 11 and 12). The metal is not released in the intestine to a significant extent.

For oral in vivo application the soluble metal oxyhydroxide-polyol complexes are encapsulated or provided with an acid-resistant coating so that an undesired release of iron(III) ions by the acidic gastric juice cannot take place. Furthermore for in vivo application the $\alpha$ 1–4 glycosidic bonds and $\alpha$ 1–6 glycosidic bonds in support materials based on carbohydrates are modified by reaction with the metal oxyhydroxide in order to avoid an undesired enzymatic degradation.

The chemical modification of the aforementioned adsorbents is exemplified by the preferred embodiment using iron(III) salts (see production examples 1–3): trivalent iron as a central atom coordinatively binds six water molecules in aqueous solution. One or several of these water molecules are exchanged under strongly alkaline conditions (pH greater than 10) for a functional OH group of the support material. This process leads to the coordinative binding of iron(III)-aquo complexes onto the support surface. In addition the strongly alkaline environment favours the deprotonation of the water coordinatively bound to the central iron atom. The deprotonated water molecules then form $O^{2-}$ bridges between two neighbouring central iron atoms. This process leads to a three dimensional linking of the iron-aquo complexes. A network of polynuclear (multinuclear) iron (III) oxyhydroxide complexes bound to the support surface is formed.

The present invention is elucidated in more detail by the following examples in conjunction with FIGS. 1 and 2.

EXAMPLE 1

Synthesis of dextran-iron(III) complex supports 40 g dried dextran support (Pfeiffer & Langen Co. Dormagel N®25 C) is added to 200 ml iron(III) chloride solution (Merck, Darmstadt, 100 g $FeCl_3 \times 6H_2O$ adjusted to 200 ml volume with redistilled water, corresponds to a 50% solution) while stirring (paddle mixer 75 rpm). The suspension is subjected to a swelling process for ca. 12 hours, subsequently the mixture is placed in 2 l 0.7 N sodium hydroxide solution while stirring vigorously (paddle mixer 500 rpm). After stirring for 15 min it is rinsed with deionized water until the pH is 9. After a 5 minute ultrasonic treatment it is again rinsed with deionized water until a pH value of 7.5 is achieved.

The content of iron and iron(III) oxyhydroxide complexes in the support materials is determined by means of atomic absorption spectroscopy or emission spectroscopy with inductively coupled plasma.

The iron content of the supports can be altered in a specific and reproducible manner via the amount of iron(III) chloride or/and the number of cycles according to the above synthesis instructions (see Table 1).

TABLE 1

Iron content in relation to dry weight

| | Fe content (%) |
|---|---|
| Single cycle | 15.7 |
| Two cycles | 25.5 |
| Three cycles | 29.3 |

EXAMPLE 2

Synthesis of vinyl acetate copolymer-iron(III) complex supports 10 g dried vinyl acetate-hydroxycopolymer support (Biosynth; Riedel de Haen) is mixed with 20 ml of a 50% (w/w) iron (III) hexahydrate solution (Merck, Darmstadt) while stirring manually. The swelling process of the suspension takes a total of ca. 1 hour, and subsequently the synthesis mixture is subjected to a 5 minute ultrasonic treatment. The mixture is placed in 200 ml 1 N sodium hydroxide solution while stirring vigorously (paddle mixer, 500 rpm). Subsequently the iron(III) oxyhydroxide-modified support is rinsed with deionized water until a pH value of 9 is achieved, again treated with ultrasound (5 min) and adjusted to a pH value of 7.5 by rinsing with deionized water.

The content of iron(III) is 17% (determined by atomic absorption spectroscopy).

EXAMPLE 3

Synthesis of divinylbenzene copolymer-iron(III) complex support 50 g dried divinylbenzene copolymer (Lewatit R 1836/249/257–260, Bayer Co., Leverkusen) is converted into the hydroxide-activated form (shake for two hours with a two-fold "batch volume" of 96% ethanol (Merck Co., Darmstadt), after filtration add a two-fold "batch volume" of 2 N sulphuric acid (Merck co., Darmstadt) and wash after filtration). 50 g iron(III) chloride hexahydrate and 5 ml redistilled water are added to the hydroxy-activated support (50 g) and stirred manually until it is homogeneous. After a 5 minute ultrasonic treatment, the suspension is placed in 750 ml 1 N sodium hydroxide solution. After stirring for 15 minutes (paddle mixer 500 rpm), the support is rinsed with deionized water until pH 9 is achieved, treated with ultrasound (5 min) and again rinsed until a pH of 7.5 is achieved.

The iron(III) content of the supports is between 6.4 and 10% iron (measured by atomic absorption spectroscopy) depending on the species.

EXAMPLE 4

Sterilization of support materials modified with iron(III) oxyhydroxide

Adsorbent:
1. Dextran-iron(III) complex support (DI)
2. Vinyl acetate copolymer-iron(III) complex support (VA)
3. Divinylbenzene copolymer-iron(III) complex support (DVB type 260)

After synthesis the adsorber materials 1–3 are adjusted to 50 ml volume in a measuring cylinder and subsequently transferred with 100 ml water into a glass bottle which can be sealed with a rubber stopper and sterilized under $F_{015}$ heat sterilization conditions.

In parallel the adsorber materials are dried in a drying cupboard at 60° C., sealed in aluminium foil under vacuum and also heat-sterilized under $F_{015}$ conditions.

The iron content is checked before and after sterilization. The results are shown in Table 2. In none of the cases is the iron content of the supports influenced by the sterilization process.

TABLE 2

Iron content of the support materials before and after sterilization

| | Iron Content (%) in Relation to Dry Weight | | | |
|---|---|---|---|---|
| Adsorbent | Before sterilization aqueous product | After sterilization aqueous product | Before sterilization dry product | After sterilization dry product |
| 1 | 20.1 | 20.1 | 20 | 19.9 |
| 2 | 17.3 | 17.2 | 17.3 | 17.4 |
| 3 | 6.4 | 6.2 | 6.3 | 6.3 |

EXAMPLE 5

Binding capacity of the support materials according to examples 1–3 for inorganic phosphate from an aqueous phosphate solution and from dialysis fluid containing phosphate Adsorbent:
1. Dextran-iron(III) complex support (DI)
2. Vinyl acetate copolymer-iron(III) complex support (VA)
3. Ester-modified divinylbenzene copolymer-iron(III) complex support (DVB type 260)

Experimental procedure:
A. Aqueous phosphate solution (10 mg phosphorus/100 ml) Preparation:
  5.8 g/l NaCl=100 mmol/l
  0.29 g/l KCl=4 mmol/l
  0.07 g/l $Na_2SO_4$=0.5 mmol/l
  0.28 g/l $Na_2HPO_4 \times 2H_2O$=1.6 mmol/l
  0.24 g/l $NaH_2PO_4 \times 2H_2O$=1.6 mmol/l
B: Dialysis fluid: HDY 314 (B. Braun Melsungen AG) admixed with 1.6 mmol $Na_2HPO_4 \times 2H_2O$ and 1.6 mmol $NaH_2PO_4 \times 2H_2O$.

The adsorber materials (1–3) are washed with redistilled water over a G3 nutsch filter, poured into a chromatography column (Biorad 120 mm×10 mm) and subsequently equilibrated with 300 ml 50 mmol/l Tris-HCl pH 7.4 (column bed volume: 3 ml).

350 ml of solutions A or B are applied to the column at room temperature and pumped through the column (volume flow 1 ml/min). After 4 ml preeluate, fractions of 10 ml each were collected and their phosphate and phosphorus content was determined by means of a photometric phosphorus-molybdenum test.

The phosphate binding capacity in % is calculated from:

$$\text{Phosphate binding capacity} = \frac{\text{Initial concentr.} - \text{total eluate concentr.} \times 100}{\text{initial concentration}}$$

TABLE 3

Phosphate binding of the adsorbents

| Adsorbent | (%) | mg phosphate/ml | mg phosphorus/ml | mmol phosphate/ml |
|---|---|---|---|---|
| aqueous phosphate solution (A) | | | | |
| 1 | 22 | 7.58 | 2.52 | 0.081 |
| 2 | 19 | 6.65 | 2.21 | 0.071 |
| 3 | 6 | 2.1 | 0.71 | 0.022 |
| Dialysis fluid containing phosphate (B) | | | | |
| 1 | 21 | 7.35 | 2.45 | 0.079 |
| 2 | 19 | 6.65 | 2.21 | 0.071 |
| 3 | 7 | 2.45 | 0.81 | 0.026 |

Conversion factor: mg phosphorus into mg phosphate = 3.161

EXAMPLE 6

Binding capacity of the support materials for inorganic phosphate from human plasma Adsorbent:
1. Dextran-iron(III) complex support (DI)
2. Vinyl acetate copolymer-iron(III) complex support (VA)
3. Divinylbenzene copolymer-iron(III) complex support (DVB type 260)
4. Divinylbenzene copolymer-iron(III) complex support (DVB type 1836/88, particle size distribution 100–250 μm)
5. Divinylbenzene copolymer-iron(III) complex support (DVB type R 249, particle size distribution 200–500 μm)

Experimental procedure:

Analogous to example 5. 100 ml human plasma are stabilized with 3 units Na heparin (B. Braun Melsungen AG) per ml and pumped over the column. The phosphate adsorption capacities of the support species used are listed in Table 4.

TABLE 4

Binding capacity for phosphate from human plasma

| Adsorbent | % | mg phosphorus/ml | mmol phosphate/ml |
|---|---|---|---|
| 1 DI | 56 | 2.1 | 0.067 |
| 2 VA | 65 | 2.4 | 0.077 |
| 3 type 260 | 26 | 1.0 | 0.032 |
| 4 type 1836/88 | 90 | 3.4 | 0.109 |
| 5 type 249 | 50 | 1.9 | 0.061 |

Conversion factor: mg phosphorus into mg phosphate = 3.161

EXAMPLE 7

Selectivity of the adsorbents with regard to the elimination of inorganic phosphate from human plasma Adsorbent:

1. Dextran-iron(III) complex support (DI)
2. Divinylbenzene copolymer-iron(III) complex support (DVB type R 249)

Experimental procedure:

Analogous to example 6. After a dead volume of 4 ml, 10 eluate fractions each of 10 ml are collected for analysis which are then examined for parameters of human plasma which are relevant to clinical chemistry.

The results of this experiment are shown in Table 5 for adsorbent 1 and in Table 6 for adsorbent 4.

TABLE 5

Clinical-chemical parameters before and after column passage of human plasma over a dextran-iron(III) complex support (DI N25; according to example 1)

| Parameter | E1 | E2 | E3 | E4 | E5 | E6 | E7 | E8 | E9 | E10 | Init. | Conc. |
|---|---|---|---|---|---|---|---|---|---|---|---|---|
| Magnesium | 1.76 | 1.85 | 1.92 | 1.94 | 1.93 | 1.95 | 1.94 | 1.99 | 1.96 | 1.96 | 1.99 | mg/dl |
| Phosphorus | 0.9 | 1.7 | 2.2 | 2.6 | 2.8 | 2.9 | 3.1 | 3.1 | 3.2 | 3.2 | 3.3 | mg/dl |
| Sodium | 143.4 | 143.7 | 143.0 | 143.7 | 143.0 | 144.0 | 143.8 | 143.7 | 143.5 | 144.5 | 143.7 | mmol/l |
| Potassium | 3.44 | 3.51 | 3.52 | 3.54 | 3.52 | 3.54 | 3.52 | 3.52 | 3.51 | 3.54 | 3.52 | mmol/l |
| Calcium | 1.64 | 1.91 | 1.98 | 2.02 | 2.06 | 2.05 | 2.07 | 2.09 | 2.09 | 2.08 | 2.18 | mmol/l |
| Chloride | 106.8 | 105.8 | 105.7 | 106.5 | 106.0 | 106.5 | 106.3 | 106.5 | 106.3 | 106.5 | 105.8 | mmol/l |
| Iron | 98 | 99 | 98 | 98 | 98 | 97 | 98 | 98 | 98 | 98 | 96 | µg/dl |
| Ferritin | 302.6 | 248.8 | 295.9 | 247.0 | 233.0 | 298.2 | 259.4 | 259.4 | 256.4 | 297.5 | 275.3 | ng/ml |
| Transferrin | 279 | 277 | 282 | 281 | 273 | 280 | 281 | 274 | 251 | 276 | 283 | mg/dl |
| Total Protein | 7.33 | 7.58 | 7.46 | 7.49 | 7.45 | 7.41 | 7.54 | 7.51 | 7.42 | 7.53 | 7.56 | g/dl |
| Creatinine | 0.87 | 0.92 | 0.93 | 0.91 | 0.92 | 0.94 | 0.93 | 0.94 | 0.91 | 0.94 | 0.90 | mg/dl |
| Albumin | 3890 | 4110 | 3520 | 3700 | 3800 | 3940 | 3630 | 4030 | 3730 | 3720 | 3870 | mg/dl |
| IgG | 1190 | 1270 | 1300 | 1360 | 1300 | 1250 | 1330 | 1260 | 1310 | 1300 | 1260 | mg/dl |
| IgA | 296 | 295 | 262 | 297 | 306 | 302 | 308 | 312 | 312 | 307 | 312 | mg/dl |
| IgM | 114 | 119 | 118 | 121 | 114 | 126 | 119 | 115 | 122 | 114 | 122 | mg/dl |

E1–E10 = eluate 1 – eluate 10
Init. = initial value
Conc. = concentration
Conversion factor: mg phosphorus into mg phosphate = 3.161

TABLE 6

Clinical-chemical parameters before and after column passage of human plasma over a divinylbenzene-iron(III) complex support (DVB type R 249; according to example 3).

| Parameter | E1 | E2 | E3 | E4 | E5 | E6 | E7 | E8 | E9 | E10 | Init. | Conc. |
|---|---|---|---|---|---|---|---|---|---|---|---|---|
| Magnesium | 0.17 | 0.17 | 0.24 | 0.38 | 0.56 | 0.80 | 0.99 | 1.22 | 1.35 | 1.454 | 1.99 | mg/dl |
| Phosporus | 0.2 | 0.3 | 0.8 | 1.4 | 2.0 | 2.5 | 2.8 | 3.0 | 3.1 | 3.1 | 3.3 | mg/dl |
| Sodium | 142.7 | 142.8 | 142.3 | 143.1 | 143.7 | 143.8 | 143.0 | 143.5 | 144.2 | 143.1 | 143.7 | mmol/l |
| Potassium | 3.23 | 3.50 | 3.48 | 3.52 | 3.53 | 3.54 | 3.51 | 3.53 | 3.54 | 3.50 | 3.52 | mmol/l |
| Calcium | 2.57 | 2.59 | 2.5 | 2.49 | 5.48 | 2.49 | 2.46 | 2.39 | 2.63 | 2.33 | 2.18 | mmol/l |
| Chloride | 106.2 | 105.8 | 105.3 | 106.1 | 106.2 | 106.2 | 106.3 | 105.3 | 106.5 | 105.9 | 105.8 | mmol/l |
| Iron | 99 | 100 | 99 | 99 | 100 | 99 | 98 | 98 | 99 | 100 | 96 | µg/dl |
| Ferritin | 267.1 | 322.5 | 285.8 | 260.0 | 329.6 | 304.7 | 322.8 | 249.1 | 269.0 | 315.8 | 275.3 | ng/ml |
| Transferrin | 277 | 294 | 293 | 277 | 266 | 287 | 255 | 269 | 278 | 281 | 283 | mg/dl |
| Total Protein | 7.31 | 7.39 | 7.39 | 7.41 | 7.39 | 7.45 | 7.51 | 7.45 | 7.57 | 7.47 | 7.56 | g/dl |
| Creatinine | 0.90 | 0.90 | 0.86 | 0.91 | 0.89 | 0.90 | 0.89 | 0.91 | 0.94 | 0.90 | 0.90 | mg/dl |

E1–E10 = eluate 1 – eluate 10
Init. = initial value
Conc. = concentration
Conversion factor: mg phosphorus into mg phosphate = 3.161

EXAMPLE 8

Blood compatability—haemocompatability of the adsorbents

Adsorbent:
1. Dextran-iron(III) complex support (DI N25c; according to example 1)

Experimental procedure:

Phosphate elimination from heparinized whole blood

A 35 ml cartridge which is provided at both ends with a 100 µm filler is packed with adsorbent 1, rinsed with redistilled water (500 ml) and subsequently with Ringer's solution (5 IU/ml Na heparin, B. Braun Melsungen). Afterwards freshly collected heparinized whole blood (4 IU/ml heparin) is passed through the cartridge at a flow rate of 20 ml/min (530 ml) by hydrostatic pressure and 12 fractions each of 45 ml are collected and their blood counts are examined. The results of this experiment are shown in tables 7, 8 and 9.

TABLE 7

Blood count (automatic cell counting)

| Fraction (45 ml) | 2 | 4 | 6 | 8 | 10 | Initial Values | Dimension |
|---|---|---|---|---|---|---|---|
| Leucocytes | 5.2 | 5.5 | 5.4 | 4.9 | 5.1 | 6.5 | $10^9/l$ |
| Lymphocytes | 61.5 | 59.4 | 60.1 | 65.6 | 62.8 | 63.4 | % |
| Monocytes | 3.9 | 4.1 | 4.2 | 3.8 | 4.9 | 3.9 | % |
| Eosinophils | 6.1 | 6.8 | 6.2 | 6.2 | 6.3 | 6.2 | % |
| Basophils | 0.3 | 0.0 | 0.0 | 2.8 | 0.1 | 0.2 | % |
| Erythrocytes | 4.51 | 4.54 | 4.47 | 4.50 | 4.51 | 4.25 | $10^3/l$ |
| Hemoglobin | 15.2 | 15.3 | 15.3 | 15.3 | 15.3 | 14.3 | g/dl |
| Hematocrit | 43.1 | 43.1 | 43.8 | 42.5 | 43.1 | 40.7 | % |
| Mean Corpuscular Volume (MCV) | 95.5 | 96.3 | 95.0 | 95.7 | 95.4 | 95.7 | fl |
| Mean Corpuscular Hemoglobin (MCH) | 35.7 | 33.8 | 34.1 | 34.0 | 34.0 | 33.6 | pg |
| Mean Corpuscular Hemoglobin Concentration (MCHC) | 35.3 | 35.0 | 35.9 | 35.5 | 35.6 | 35.0 | g/dl |
| Thrombocytes | 122 | 122 | 134 | 89 | 91 | 226 | $10^9/l$ |
| Mean Thrombocyte Volume | 8.3 | 8.2 | 8.3 | 8.0 | 8.2 | 8.6 | fl |
| Free Hemoglobin | 1.95 | 2.01 | 2.19 | 2.20 | 2.15 | 1.55 | mg/dl |

TABLE 8

Differential blood smear

| | Initial value | Fraction 4 | Dimension |
|---|---|---|---|
| Lymphocytes | 71 | 74 | % |
| Monocytes | 1 | 4 | % |
| Eosinophils | 4 | 3 | % |
| Basophils | 5 | 1 | % |
| Stab cells | 0 | 2 | % |
| Polymorphs | 19 | 16 | % |

TABLE 9

Group test for plastic coagulation

| | Initial value | Fraction 4 | Dimension |
|---|---|---|---|
| Fibrinogen | 376 | 370 | mg/dl |
| plasminogen | 119 | 118 | % |
| antithrombin II | 105 | 102 | % |
| partial thromboplastin time (PTT) | 33 | 37 | sec. |
| thromboplastin time (Quick value) | 100 | 100 | % |

A comparison of the parameters before and after contacting the plasma or blood with the adsorbent material according to the present invention shows that the coagulation system is not influenced in an undesirable manner by the treatment.

EXAMPLE 9

In vitro circulation experiment of human blood over a pump-driven cartridge system The aim of the experiment is to examine the capacity to withstand hydraulic loads and pressure behaviour of human blood which has been recirculated several times over a cartridge filled with the phosphate adsorber according to the present invention as described in examples 1 and 2.

Adsorbent:
1. Dextran-iron(III) complex support (DI)
2. Vinyl acetate copolymer-iron(III) complex support (VA)

Figure 1:
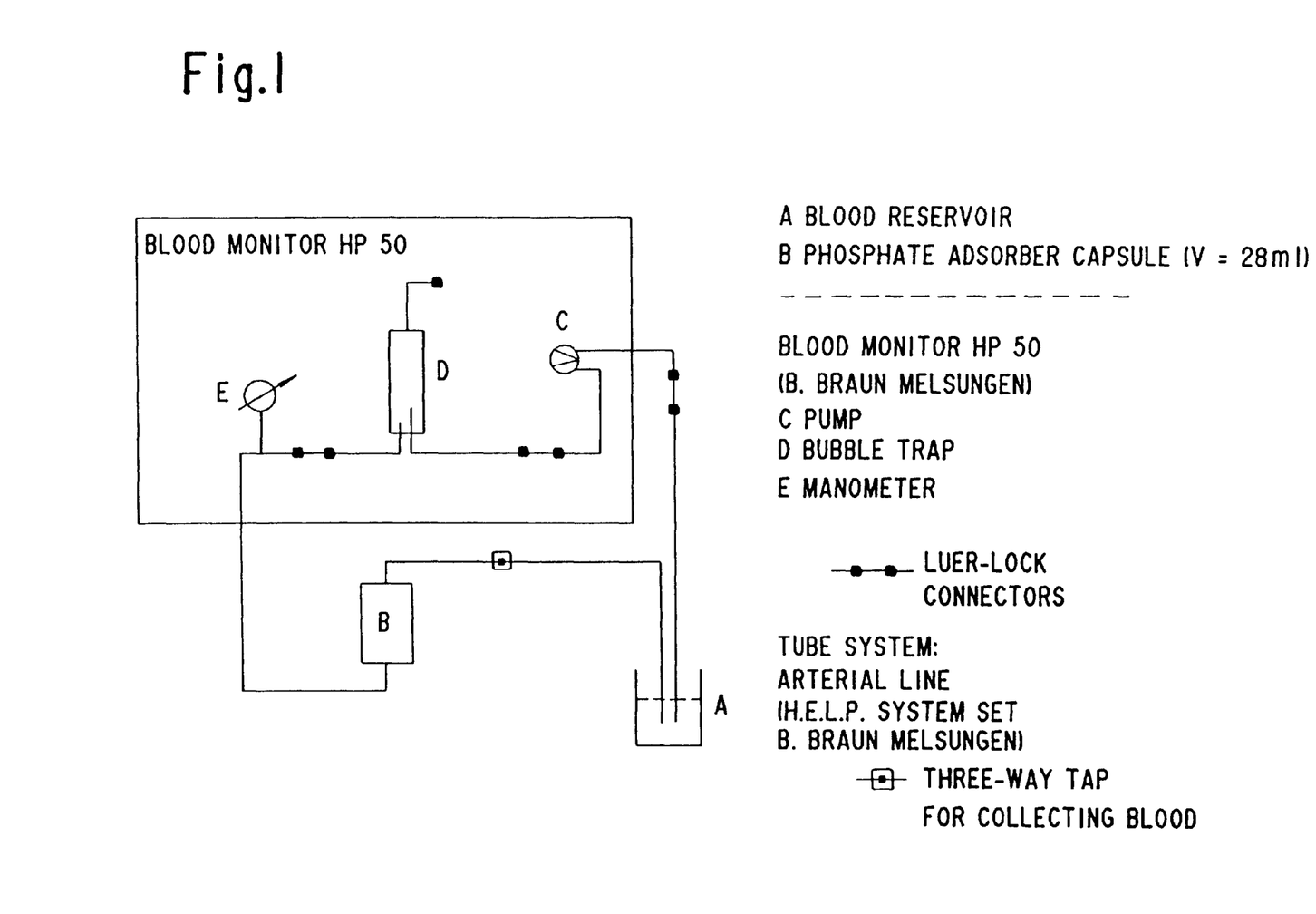
FIG. 1 shows a diagram of an apparatus for removing inorganic phosphate from human blood.

Experimental procedure:

A cylindrical capsule (diameter 55 mm, volume 28 ml with an integrated sieve fabric—pore size 92 µm) is in each case loaded with heat-sterilized adsorbent 1 or 2 and equilibrated with 1.5 l 50 mmol/l Tris-HCl buffer pH 7.4 (50 ml/min, 20 mm Hg). After rinsing the system with 1.5 l physiological saline, 350 ml human blood, to which 6 units Na heparin (B. Braun Melsungen AG) per ml have been added, is fed into the circulation process (see sketch 1). The entire added blood volume is in each case continuously pumped over the cartridge and through the tubing system at a volume flow of 50 ml/min in exchange cycles until haemolysis occurs. The sampling (1 ml human blood) is carried out via a three way tap (see FIG. 1) after each exchange cycle.

The collected blood fractions are examined for their phosphate content as well as for their haemolysis activity. The results of the experiment are shown in Table 10. After 5 or 25 exchange cycles the values for the eluates exceed the limit for haemodialysis (DIN 58352) of an absorbance of $A \geq 0.03$. Adsorbent 2 has a particle-size distribution of 50–200 µm which proves to be disadvantageous for the capacity to withstand hydraulic loads and for the pressure behaviour of human blood.

TABLE 10

Circulation experiment with human blood

| Material | Phosphate adsorption (%) | Pressure mm Hg | Number of exchange cycles until haemolysis occurs |
|---|---|---|---|
| Adsorbent 1: | | | |
| dextran support 150–300 μm | 90 | 44 | 25 |
| Adsorbent 2: | | | |
| VA support 50–200 μm | 90 | 50 | 5 |

EXAMPLE 10

Comparative investigation of the release of iron(III) ions from adsorbent materials by liquids containing protein Adsorbent:
1. according to example 1
2. iminodiacetic acid cation exchanger loaded with iron (III) (Lewatit R 251 K, Bayer AG Co. Leverkusen) according to the state of the art The copolymer of styrene and divinylbenzene functionalized with iminodiacetic acid corresponds to adsorbent No. 1 in DE 28 15 811. The cation exchanger was firstly converted into the H$^+$ form with 1 N HCl, saturated with a 50 mmol/l iron(III) chloride solution and subsequently washed with redistilled water.

Experimental procedure:
10 ml human serum is applied to a column packed with the respective absorbent (2 ml column bed volume) and equilibrated with Ringer's solution. The first 1 ml fraction is discarded (dilution effects) and the content of iron is determined in the remaining 1 ml fractions.

TABLE 11

Release of iron(III) ions

| | | Adsorbent 1 | Adsorbent 2 |
|---|---|---|---|
| Iron (μg/100 ml) | initial value | 60 | 60 |
| Iron (μg/100 ml) | fraction 1 | 56 | 165 |
| | 2 | 62 | 170 |
| | 3 | 65 | 183 |
| | 4 | 60 | 198 |
| | 5 | 63 | 202 |
| | 6 | 66 | 214 |
| | 7 | 59 | 225 |
| | 8 | 66 | 245 |
| | 9 | 65 | 274 |

The values obtained clearly show an undesired release of iron(III) ions by serum proteins when using an adsorbent according to DE 28 15 811 whereas no significant release of iron(III) ions takes place with the adsorbent according to the present invention.

EXAMPLE 11

Elimination of inorganic phosphate by soluble metal oxyhydroxide/polyol complexes from aqueous phosphate solutions Adsorbent:
1. Ferrum® juice (Hausmann Co. St. Gallen) (HS)
2. Dormapher® solution (Pfeiffer-Langen, Dormagen) (PL)

Figure 2:
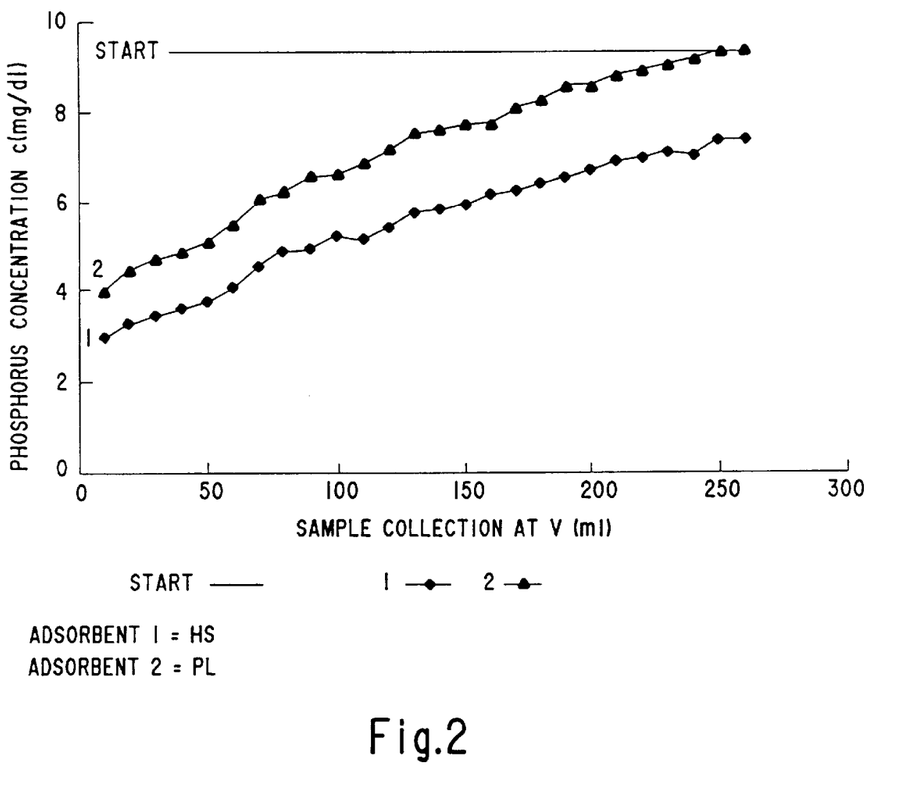
FIG. 2 shows the elimination of inorganic phosphate by soluble metal oxyhydroxide-polyol complexes from aqueous phosphate solutions.

Experimental procedure:
Aqueous phosphate solution (10 mg phosphorus/100 ml)
Preparation:
5.8 g/l NaCl=100 mmol/l
0.29 g/l KCl=4 mmol/l
0.07 g/l Na$_2$SO$_4$=0.5 mmol/l
0.28 g/l Na$_2$HPO$_4$×2H$_2$O=1.6 mmol/l
0.24 g/l NaH$_2$PO$_4$×2H$_2$O=1.6 mmol/l
40 ml of each adsorbent 1 and 2 is in each case loaded into an ultrafiltration unit (stirred cell 8200/Amicon, pressure 3 bar) and the above phosphate solution is added continuously. The metal oxyhydroxide-polyol complexes which adsorb the phosphate ions are retained by the membrane (Filtron Omega NM BL 3K). The eluted solution is collected in 10 ml fractions after 40 ml preeluate and their phosphate/phosphorus concentration is determined according to example 5. FIG. 2 shows the elimination of inorganic phosphate achieved by soluble metal oxyhydroxide/polyol complexes from aqueous phosphate solutions.

EXAMPLE 12

Binding capacity of soluble metal oxyhydroxide-polyol complexes for inorganic phosphate from standardized intestinal contents Adsorbent:
1. Ferrum® juice (Hausmann Co., St. Gallen) (HS)
2. Ferrum® drops (Hausmann Co., St. Gallen) (HT)
3. Dormapher® solution (Pfeiffer-Langen Co., Dormagen) (PL)

Experimental procedure:
Standardized intestinal contents
Preparation:
6.8 g/l KH$_2$PO$_4$=50 mmol/l
10 g/l pancreatin
pH 7.5
50 ml of each of the adsorbents 1–3 is mixed in each case with 1 liter of the above solution, poured into dialysis tubes (NMWL 1K Spetropor), dialysed for 72 hours against water and the phosphate/phosphorus concentration in the dialysate is determined according to example 5.

TABLE 12

Phosphorus adsorption by soluble metal oxyhydroxide-polyol complexes from standardized intestinal contents

| Adsorbent | amount of bound phosphate (mg) | amount of bound phosphorus (mg)/ml adsorbent |
|---|---|---|
| 1 (HS) | 6 | 0.12 |
| 2 (HT) | 38 | 0.76 |
| 3 (PL) | 16.5 | 0.33 |

What is claimed is:

1. Method of treating hyperphosphatemia comprising administering to a subject which is in need thereof an aqueous insoluble composition comprising a polynuclear metal oxyhydroxide bound to an adsorbent base material, wherein the polynuclear metal oxyhydroxide is a polynuclear oxyhydroxide of iron, zirconium or aluminum.

2. The method of claim 1 wherein said adsorbent base material comprises hydroxyl groups which are reactive with said polynuclear metal oxyhydroxide.

3. The method of claim 1 wherein said composition is a particulate solid.

4. The method of claim 1 wherein said composition has an average particle size of about 5 to 500 μm.

5. The method of claim 1 wherein said adsorbent base material comprises an aqueous insoluble polyhydroxy compound.

6. The method of claim 1 wherein said adsorbent base material comprises an at least partially aqueous soluble polyhydroxy compound.

7. The method of claim 1 wherein said adsorbent base material is at least one member selected from the group consisting of a silicate, silicon dioxide, glyceryl modified silica gel, glyceryl modified glass and a polymer.

8. The method of claim 7 wherein said polymer comprises a polysaccharide.

9. The method of claim 7 wherein said polymer is an organic polymer.

10. The method of claim 7 wherein said polymer is a cross-linked carbohydrate.

11. The method of claim 1 wherein said adsorbent base material is at least one member selected from the group consisting of agarose, dextran, dextrin, cellulose and polyvinyl alcohol.

12. The method of claim 1 wherein said administering is orally.

13. The method of claim 12 wherein said composition has an average particle size of about 5 to 200 microns.

14. The method of claim 1 wherein said polynuclear metal oxyhydroxide is Fe (III) oxyhydroxide.

15. The method of claim 1 wherein the iron content based on the dry weight of the composition is from about 6.3 to 29.3%.

16. The method of claim 1 wherein said composition has a phosphorus binding capacity based on the volume of a wet composition of up to 3.4 mg phosphorus per ml composition.

17. The method of claim 1 wherein said subject is a human.

* * * * *